US008329952B2

(12) United States Patent
Jetti et al.

(10) Patent No.: US 8,329,952 B2
(45) Date of Patent: Dec. 11, 2012

(54) PROCESS FOR THE PREPARATION OF O-DESMETHYLVENLAFAXINE SUCCINATE POLYMORPHIC FORMS

(75) Inventors: Ramakoteswara Rao Jetti, Secunderabad (IN); Purandhar Koilkonda, Secunderabad (IN); Jagan Mohana Chary Tummanapally, Secunderabad (IN); Mohana Vamsi Krishna Vadlamudi, Secunderabad (IN); Prasanth Kumar Barik, Secunderabad (IN); Om Dutt Tyagi, Secunderabad (IN)

(73) Assignee: Matrix Laboratories Limited, Andhra Pradesh (IN)

( * ) Notice: Subject to any disclaimer, the term of this patent is extended or adjusted under 35 U.S.C. 154(b) by 372 days.

(21) Appl. No.: 12/669,487

(22) PCT Filed: Jul. 15, 2008

(86) PCT No.: PCT/IN2008/000450
§ 371 (c)(1),
(2), (4) Date: Mar. 11, 2010

(87) PCT Pub. No.: WO2009/010990
PCT Pub. Date: Jan. 22, 2009

(65) Prior Publication Data
US 2010/0191015 A1 Jul. 29, 2010

(30) Foreign Application Priority Data
Jul. 16, 2007 (IN) .......................... 1519/CHE/2007

(51) Int. Cl.
*C07C 211/00* (2006.01)
(52) U.S. Cl. ...................................... 564/336; 564/409
(58) Field of Classification Search .................. 564/336, 564/409
See application file for complete search history.

(56) References Cited

U.S. PATENT DOCUMENTS

| 4,535,186 | A | 8/1985 | Husbands et al. |
| 6,197,828 | B1 | 3/2001 | Jerussi et al. |
| 6,673,838 | B2 | 1/2004 | Hadfield et al. |
| 6,689,912 | B2 | 2/2004 | Weber |
| 2003/0045583 | A1 | 3/2003 | Hadfield et al. |
| 2005/0197392 | A1 | 9/2005 | Jerussi et al. |

FOREIGN PATENT DOCUMENTS
WO 03/048104 6/2003

*Primary Examiner* — Shawquia Young
(74) *Attorney, Agent, or Firm* — Workman Nydegger

(57) ABSTRACT

The present invention relates to process for the preparation of novel crystalline Desmethylvenlafaxine succinate polymorphic Forms-A, B. The present invention also relates to novel processes for the preparation of 0-Desmethylvenlafaxine succinate polymorphic Forms-(I), (II), (III) and amorphous.

4 Claims, 4 Drawing Sheets

PROCESS FOR THE PREPARATION OF O-DESMETHYLVENLAFAXINE SUCCINATE POLYMORPHIC FORMS

FIELD OF INVENTION

The present invention relates to process for the preparation of novel crystalline Desmethylvenlafaxine succinate polymorphic Forms-A, B. The present invention also relates to novel processes for the preparation of O-Desmethylvenlafaxine succinate polymorphic Forms-I, II, III and amorphous. The present invention further relates to simple and improved process for the O-demethylation of Venlafaxine

BACKGROUND OF THE INVENTION

O-Desmethylvenlafaxine succinate is a novel salt form of isolated major active metabolite of venlafaxine and has been shown to inhibit norepinephrine and serotonin uptake. O-Desmethylvenlafaxine chemically named as 1-[2-(dimethylamino)-1-(4-phenopethyl]cyclohexanol having the following structure

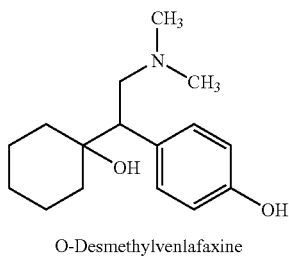

O-Desmethylvenlafaxine

U.S. Pat. No. 4,535,186 patent is filed on Oct. 26, 1983, this application has been granted on Aug. 13, 1985 and assigned to American Home Products corporation. In this application, process for the preparation of Desmethylvenlafaxine is disclosed and claimed, wherein 1-[1-(4-benzyloxyphenyl)-2-(dimethylamino)ethyl]cyclohexanol is subjected to hydrogenation reaction in the presence of 10% Palladium carbon followed by workup to give O-Desmethylvenlafaxine, which is further converted to fumarate salts by conventional methods.

In U.S. Pat. No. 6,673,838 patent application claimed different polymorphic forms of O-Desmethylvenlafaxine succinate and discloses the process for the preparation of Form-I, II, III, IV and amorphous.

Venlafaxine base is used as starting material in the preparation of O-Desmethylvenlafaxine, as demonstrated in U.S. Pat. No. 6,689,912, U.S. Pat. No. 6,197,828 WO 03/048104 and US 2005/0197392.

We have carried out the crystallization of O-Desmethylvenlafaxine succinate in a different solvents, mixture of solvents and applying different parameters to obtain a novel process for the preparation of O-Desmethylvenlafaxine succinate polymorphic Forms.

OBJECT OF THE INVENTION

The main object of the present invention is novel process for the preparation of O-Desmethylvenlafaxine succinate polymorphic form-A, B.

Yet another object of the present invention is simple and improved process for the preparation of O-Desmethylvenlafaxine succinate polymorphic form-I, II, III and amorphous.

Further object of the present invention is novel process for O-demethylation of venlafaxine.

SUMMARY OF THE INVENTION

The present invention relates to novel process for the preparation of O-Desmethylvenlafaxine succinate polymorphic Forms, which are designated as Form-A and Form-B. The present invention is also relates to novel process for the preparation of Form I, Form II, Form III and amorphous form. The present invention further relates to simple process for O-demethylation of venlafaxine.

DETAILED DESCRIPTION OF THE INVENTION

The present invention relates to novel process for the preparation of crystal forms of O-Desmethylvenlafaxine succinate, which are designated as Form-A and Form-B. The present invention further relates to novel process for the preparation of Form I, Form II, Form III and amorphous. The present invention is also relates to simple process for O-demethylation of venlafaxine to give O-Desmethylvenlafaxine base.

Figure 1:
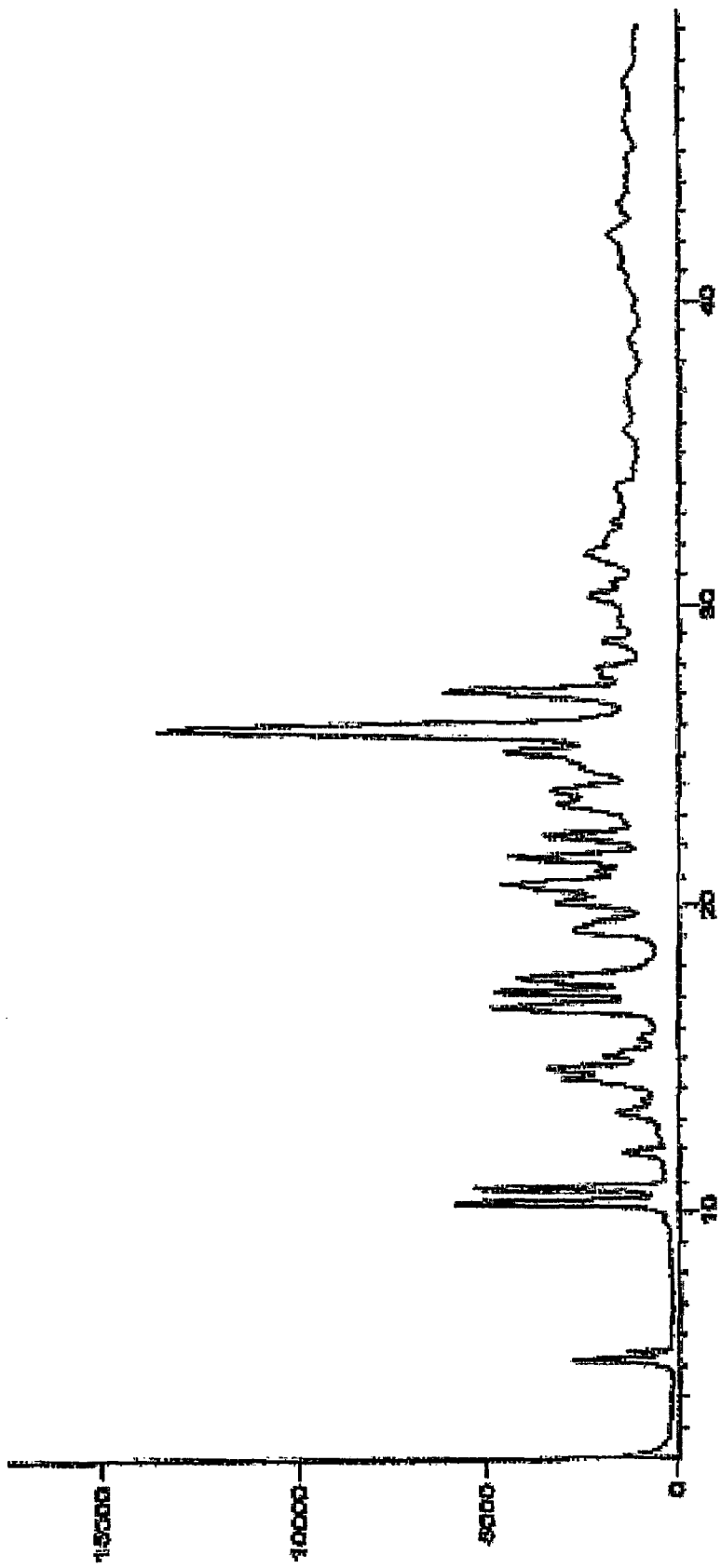
FIG. 1 is X-ray powder diffraction pattern of O-Desmethylvenlafaxine succinate Form-A.
Figure 2:
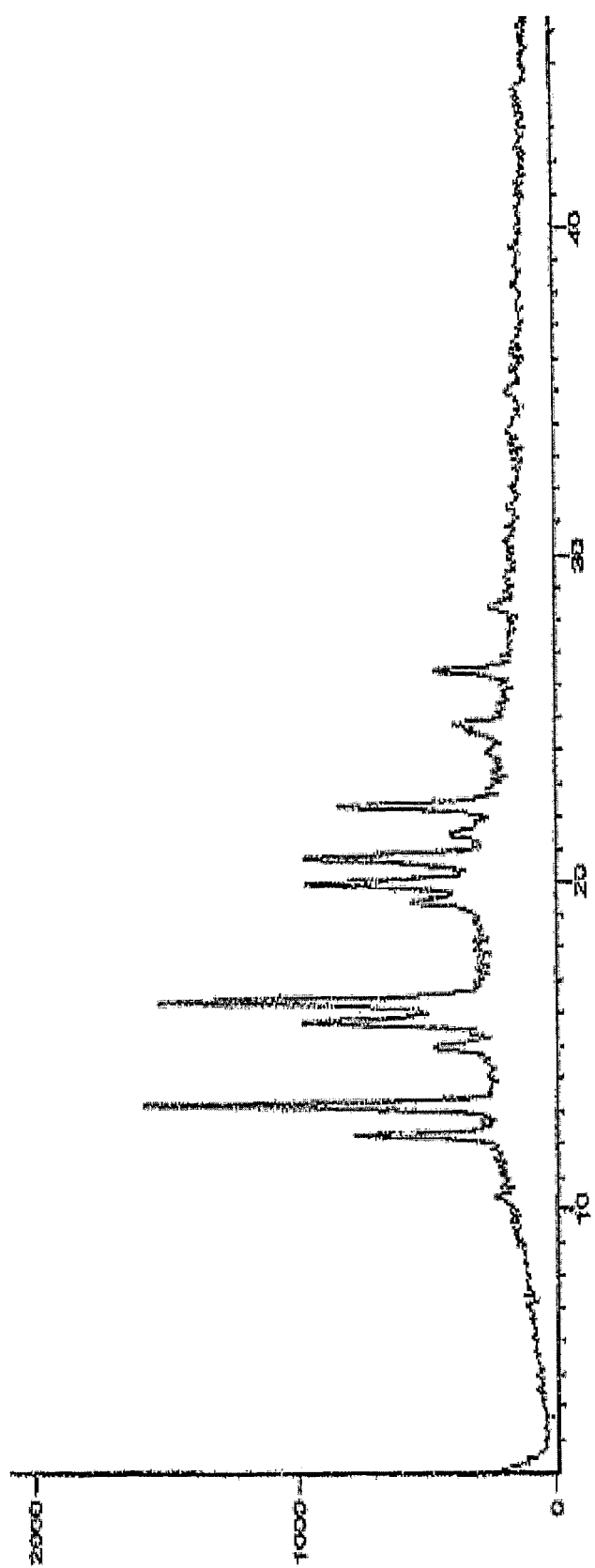
FIG. 2 is X-ray powder diffraction pattern of O-Desmethylvenlafaxine succinate Form-B.
Figure 3:
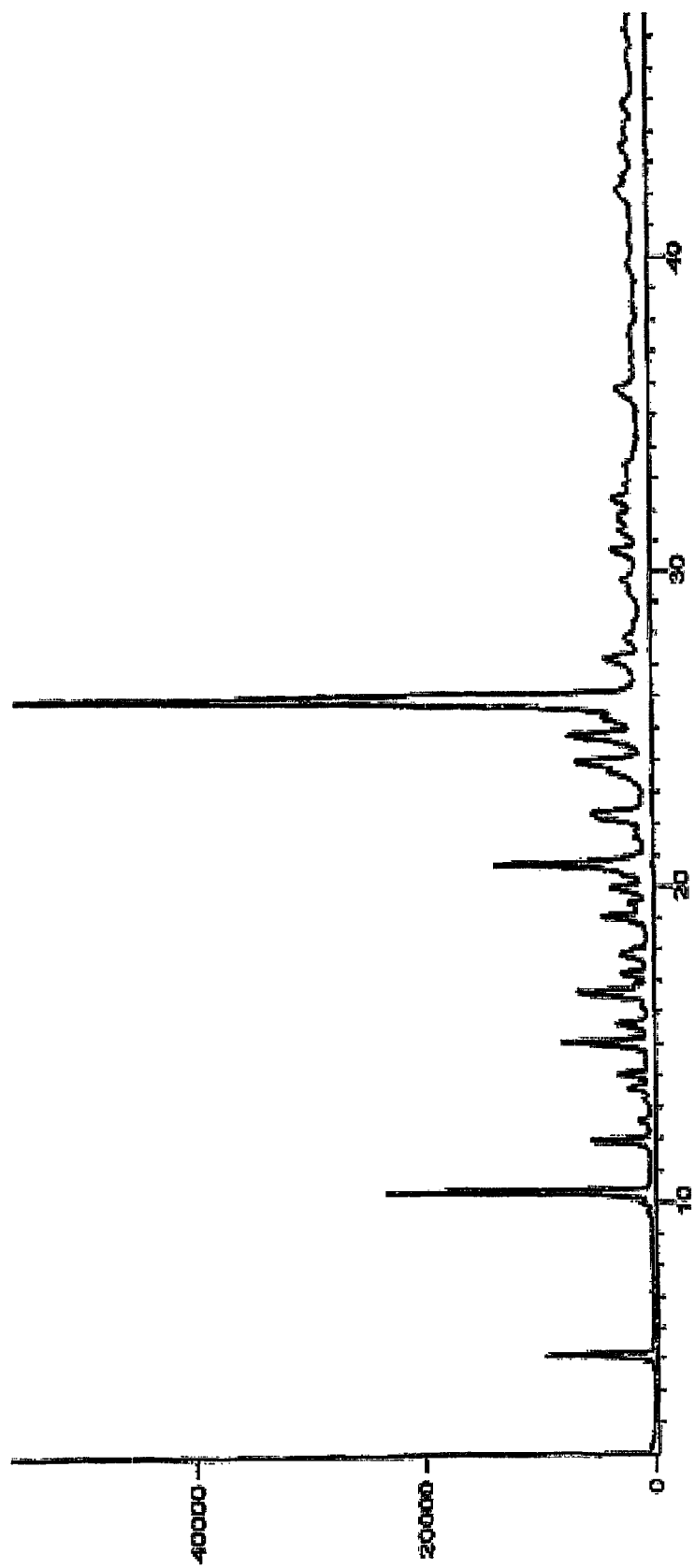
FIG. 3 is X-ray powder diffraction pattern of O-Desmethylvenlafaxine succinate Form-I.
Figure 4:
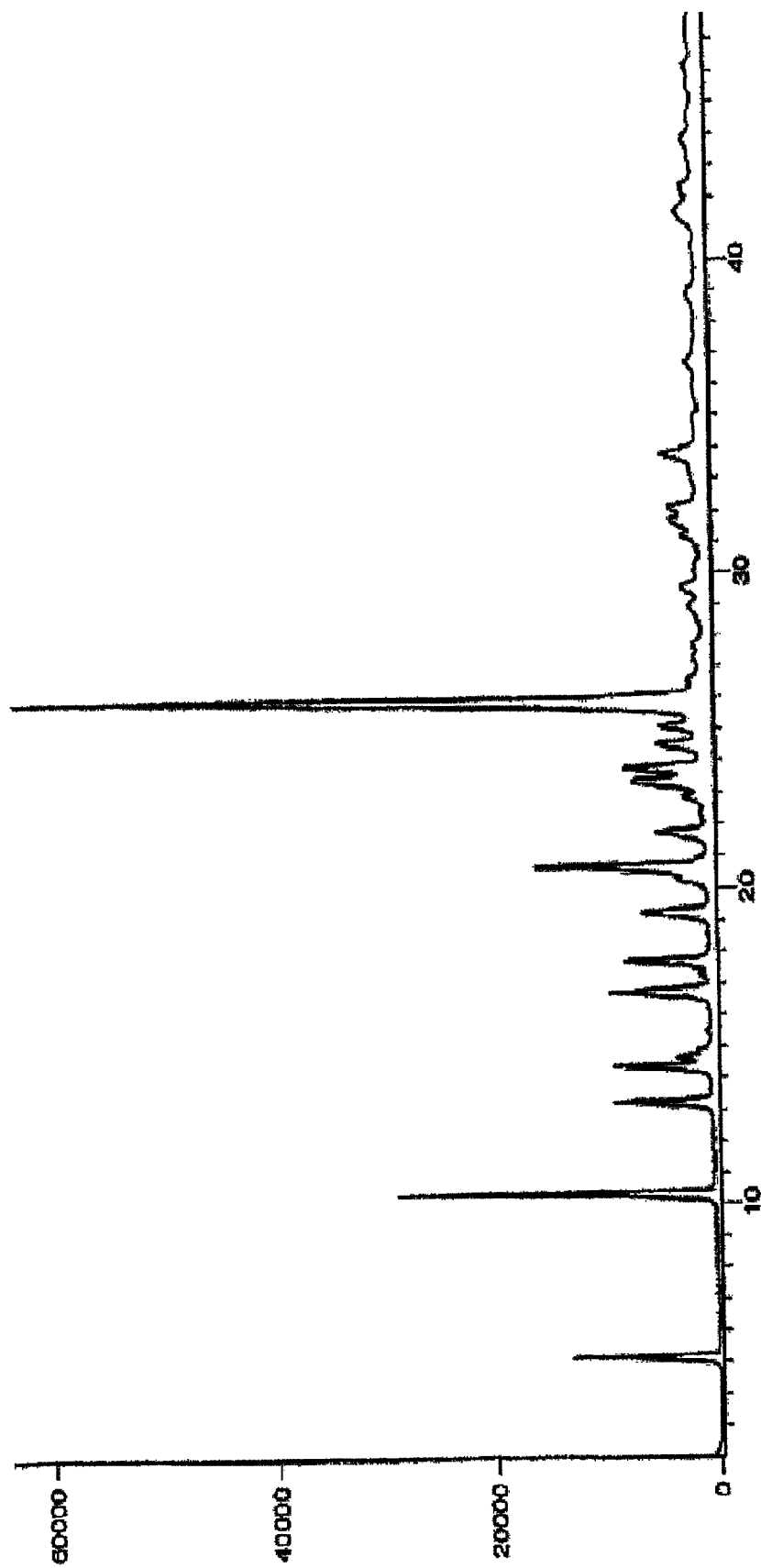
FIG. 4 is X-ray powder diffraction pattern of O-Desmethylvenlafaxine succinate Form-II.

The present invention relates to novel crystal forms of O-Desmethylvenlafaxine succinate, which are designated as Form-A and Form-B. These novel forms are characterized by X-ray powder diffraction. X-ray powder diffraction of Form-A and Form-B is shown in FIG. 1 and FIG. 2 respectively.

Powder X-Ray Diffraction (PXRD)

The PXRD measurements were carried out using PANalytical, X'Pert PRO powder diffractometer equipped with goniometer of θ/θ configuration and X'Celerator detector. The Cu-anode X-ray tube is operated at 40 kV and 30 mA. The experiments were conducted over the 2θ range of 2.0°-50.0°, 0.030° step size and 50 seconds step time.

According to the present invention, process for the preparation of O-Desmethylvenlafaxine Form-A, which comprising the steps of:

a) suspending O-Desmethylvenlafaxine succinate in a solvent medium, b) removing water by azeotropic distillation and c) isolating O-Desmethylvenlafaxine succinate Form-A.

O-Desmethylvenlafaxine succinate is suspended in a solvent system selected from the group comprising of chlorinated hydrocarbons such as dichloromethane, chloroform, dichloro ethane. The water is removed by azeotropic distillation followed by cooling and filtration to give O-Desmethylvenlafaxine succinate Form-A.

According to the present invention, process for the preparation of O-Desmethylvenlafaxine Form-B, which comprising the steps of:

a) heating O-Desmethylvenlafaxine succinate Form-A and b) isolating O-Desmethylvenlafaxine succinate Form-B.

According to the present invention, O-Desmethylvenlafaxine succinate Form-A is dried in static dryer at 60-90° C. to give O-Desmethylvenlafaxine succinate Form-B.

According to our present invention, O-Desmethylvenlafaxine succinate polymorphic form-B is also prepared by heating crystalline O-Desmethylvenlafaxine succinate polymorphic forms such as Form-I, II, III and IV at about 80° C. to 120° C. for several days to give O-Desmethylvenlafaxine succinate Form-B.

According to our present invention, O-Desmethylvenlafaxine base and succinic acid is used directly as a solid or by dissolving in a respective solvents for preparation of O-Desmethylvenlafaxine succinate polymorphic forms.

According to our present invention, Process for the preparation of O-Desmethylvenlafaxine succinate Form-I which comprising the steps of:
a) suspending O-Desmethylvenlafaxine base in a solvent,
b) heating to get a solution,
c) adding succinic acid solution to step b,
d) cooling the reaction mass and
e) isolating O-Desmethylvenlafaxine succinate Form-I.

According to our present invention, O-Desmethylvenlafaxine base is suspended in a solvent selected from aprotic polar solvents such as tetrahydrofuran, acetone, acetonitrile or mixture thereof. The resulting reaction mass is heated to 40-90° C. to get a clear solution. Succinic acid dissolved in a solvent selected from aprotic polar solvents such as tetrahydrofuran, acetone, acetonitrile or mixture thereof is added slowly to reaction mass at reflux temperature followed by cooling to room temperature. The resulting reaction mass is filtered to give O-Desmethylvenlafaxine succinate Form-I.

The present invention provides a process for preparing prior art Forms such as I, II, III, and amorphous forms of O-Desmethylvenlafaxine succinate using different solvents selected from the group comprising of alcohols, aprotic polar solvents, lower aliphatic ketones, nitro alkane, ethers, aromatic hydrocarbons, hetero aromatics, amides, water or mixtures thereof using different parameters to give crystalline O-Desmethylvenlafaxine Succinate Form I.

The solvents according to our present invention are selected from methanol, isopropyl alcohol, tetrahydrofuran, dimethylformamide, dimethylsulfoxide, acetonitrile, acetone, nitromethane, isopropyl ether, toluene, xylene, toluene, water or mixtures thereof.

According to our present invention, process for the preparation of O-Desmethylvenlafaxine succinate Form-I, which comprising the steps of:
a) suspending O-Desmethylvenlafaxine base and succinic acid in a solvent,
b) heating the reaction mass,
c) cooling the reaction mass and
d) isolating O-Desmethylvenlafaxine succinate Form-I.

According to our present invention, O-Desmethylvenlafaxine base and succinic acid is suspended in a solvent selected from aprotic polar solvents such as tetrahydrofuran, acetone, acetonitrile or alcohols such as isopropyl alcohol or mixture thereof. The reaction mass is heated to 40-90° C. to get solution, which is cooled to room temperature gradually or rapidly cooling to −10 to −45° C. gives O-Desmethylvenlafaxine succinate Form-I.

According to our present invention, process for the preparation of O-Desmethylvenlafaxine succinate Form-I, which comprising the steps of:
a) suspending O-Desmethylvenlafaxine base and succinic acid in a solvent,
b) heating the reaction mass,
c) adding anti-solvent and
d) isolating O-Desmethylvenlafaxine succinate Form-I.

According to our invention, O-Desmethylvenlafaxine base and succinic acid is suspended in a solvent selected from aprotic polar solvents such as tetrahydrofuran, acetonitrile, acetone, dioxane, dimethylformamide or aromatic hydrocarbons such as xylene, toluene or mixture thereof. The reaction mass is heated to obtain a clear solution. The clear solution is diluted with anti-solvent, selected from isopropyl ether, acetone, acetonitrile, tetrahydrofuran or mixture thereof followed by cooling and isolation to give O-Desmethylvenlafaxine succinate Form-I.

According to our present invention, process for the preparation of O-Desmethylvenlafaxine succinate Form-I, which comprising the steps of:
a) suspending O-Desmethylvenlafaxine base in solvent,
b) adding succinic acid to step a,
c) heating the reaction mass,
d) evaporating the solvent rapidly and
e) isolating crystalline O-Desmethylvenlafaxine succinate Form-I.

According to our invention, O-Desmethylvenlafaxine base is suspended in a solvent selected from tetrahydrofuran, acetonitrile, acetone, dioxane, dimethylformamide or mixture thereof. Succinic acid is added to the reaction mass followed by heating the reaction mass to 50-110° C. to obtain a clear solution. The reaction mass is subjected to rapid evaporation to give O-Desmethylvenlafaxine succinate Form-I.

According to our present invention, process for the preparation of O-Desmethylvenlafaxine succinate Form-II which comprising the steps of:
a) suspending O-Desmethylvenlafaxine base and succinic acid in a solvent,
b) heating the reaction mass,
c) cooling the reaction mass and
d) isolating O-Desmethylvenlafaxine succinate Form-II.

According to our invention, O-Desmethylvenlafaxine base and succinic acid is suspended in a solvent selected from methanol, isopropyl alcohol, acetone, 1,4-dioxane, acetonitrile, water or mixture thereof. The resulting reaction mass is heated to 50-130° C. to obtain a clear solution. The reaction mass is cooled to isolate O-Desmethylvenlafaxine succinate Form-II.

According to our present invention, process for preparing prior art Form II of O-Desmethylvenlafaxine Succinate which comprises dissolving O-Desmethylvenlafaxine succinate in a solvent or mixture of solvent, cooling the reaction mass to lower temperature and isolating O-Desmethylvenlafaxine succinate Form-II.

The O-Desmethylvenlafaxine Succinate is dissolved in a solvent selected from the group comprising of alcohols, aprotic polar solvents, esters, lower aliphatic ketones, aromatic hydrocarbons, hetero aromatics, amides, aliphatic hydrocarbons, water or mixtures thereof using different parameters to obtain crystalline O-Desmethylvenlafaxine Succinate Form II. The alcohol is selected from methanol, isopropyl alcohol, n-propanol, n-butanol, chloroform, dichloromethane, acetonitrile, dioxane, ethyl acetate, cyclohexane, water or mixtures thereof.

According to our present invention, process for the preparation of O-Desmethylvenlafaxine succinate Form-II which comprising the steps of:
a) dissolving O-Desmethylvenlafaxine base in a solvent,
b) heating the reaction mass to reflux,
c) adding succinic acid solution,
d) cooling the reaction mass and
e) isolating O-Desmethylvenlafaxine succinate Form-II.

According to our present invention, O-Desmethylvenlafaxine succinate Form-II is prepared by dissolving O-Desmethylvenlafaxine base in a solvent selected from acetonitrile, chloroform, ethyl acetate, isopropyl alcohol, n-propanol, n-butanol, cyclohexane or mixture thereof. The resulting reaction mass is heated to 50-130° C. to obtain a clear solution. Succinic acid dissolved in a solvent selected from acetonitrile, chloroform, ethyl acetate, isopropyl alcohol, n-propanol, n-butanol, cyclohexane or mixture thereof is added to the reaction mass at reflux temperature. Optionally Succinic acid is used as such with out dissolving in a solvent. The reaction mass is then cooled to 20-35° C. and isolated to give O-Desmethylvenlafaxine succinate Form-II.

According to our invention, process for the preparation of O-Desmethylvenlafaxine succinate Form-II which comprising the steps of:

a) suspending amorphous O-Desmethylvenlafaxine succinate in a solvent, b) isolating O-Desmethylvenlafaxine succinate Form-II.

According to our invention, amorphous O-Desmethylvenlafaxine succinate is suspended in a solvent selected from acetonitrile, dichloromethane, dioxane, tetrahydrofuran, dimethylformamide, dimethyl sulfoxide, acetone or mixture thereof and filtered to give O-Desmethylvenlafaxine succinate Form-II.

According to our present invention, process for the preparation of O-Desmethylvenlafaxine succinate Form-II which comprises exposing amorphous O-Desmethylvenlafaxine succinate to humidity and isolating O-Desmethylvenlafaxine succinate Form-II.

In another aspect of the present invention for preparing prior art O-Desmethylvenlafaxine Succinate Form-III which comprising the steps of:

a) suspending free base and succinic acid in a suitable solvent, b) heating to obtain a solution, c) cooling to 25-30° C. followed by addition of an anti solvent and d) isolating the O-Desmethylvenlafaxine Succinate Form-III.

O-Desmethylvenlafaxine base and succinic acid is suspended in a solvent selected from toluene, acetonitrile, acetone, or mixtures thereof and is heated to reflux to obtain a clear solution. The reaction mass is cooled to ambient temperature preferably 25-30° C. followed by dilution with anti-solvent and filtration to give O-Desmethylvenlafaxine succinate Form-III.

The present invention also provides a process for preparing prior art amorphous form of O-Desmethylvenlafaxine Succinate comprising the step of suspending O-Desmethylvenlafaxine free base and succinic acid in ethanol, methanol, acetonitrile or mixtures thereof followed by distillation, and recovering the amorphous form of O-Desmethylvenlafaxine Succinate.

The present invention further provides process for the preparation of O-Desmethylvenlafaxine which comprises the steps of dissolving venlafaxine in a solvent followed by treating with a demethylating agent such as sodium cyanide followed by isolation to give O-Desmethylvenlafaxine base.

The following non-limiting examples illustrate specific embodiments of the present invention. They are, not intended to be limiting the scope of present invention in any way.

EXAMPLE 1

Preparation of O-Desmethylvenlafaxine Succinate Form-A

In a three-necked round bottom flask (100 ml) was equipped with a reverse dean stark condenser and thermometer, O-Desmethylvenlafaxine Succinate (2 g) was suspended in methylene dichloride (50 ml). The solution was then refluxed for 3.5 hrs, cooled to about 5-10° C. The mixture was stirred at this temperature for about 30 min, filtered and dried at ambient temperature.

EXAMPLE 2

Preparation of O-Desmethylvenlafaxine Succinate Form-B 1 g of the O-Desmethylvenlafaxine Succinate Form-A obtained as described in example-1 was dried in a static dryer under vacuum at 80° C. to give O-Desmethylvenlafaxine Succinate Form B.

EXAMPLE 3

Preparation of O-Desmethylvenlafaxine Succinate Form-I 5 g of O-Desmethylvenlafaxine free base was suspended in indicated solvents at indicated volumes at 25-30° C. and stirred for 10 minutes. This slurry was heated to reflux temperature for complete dissolution. In another flask (2.8 g) of succinic acid was dissolved in indicated solvents at indicated volumes at 25-30° C. and slowly added to the free-base solution at reflux temperature and maintained for 1-3 hrs. The reaction mass was then cooled to room temperature. The solid obtained was filtered to give crystalline O-Desmethylvenlafaxine Succinate Form-I. The specific reaction conditions and results obtained are displayed in below table.

| Input | Solvents | Volume ratio | Temp. (° C.) | Time | Result |
|---|---|---|---|---|---|
| Free base and Succinic acid | THF | 1:20 | 60-70 | 1 hr | Form I |
| | Acetone | 1:40 | 50-60 | 1 hr | Form I |

EXAMPLE 4

Preparation of O-Desmethylvenlafaxine Succinate Form-I 1 g of O-Desmethylvenlafaxine free base and 0.45 g of succinic acid was suspended in indicated solvents at indicated volumes at 25-30° C. and stirred for 10 minutes. This slurry was heated for complete dissolution and allowed for crystallization at room temperature. The specific reaction conditions and results obtained are displayed in below table.

| Process | Solvents | Total volume | Volume ratio | Temp (° C.) | Result |
|---|---|---|---|---|---|
| Slow Crystallization | Acetone | 30 | 1:30 | 50-60 | Form I |

EXAMPLE 6

Preparation of O-Desmethylvenlafaxine Succinate Form-I 1 g of O-Desmethylvenlafaxine free base and 0.45 g of succinic acid was suspended in indicated solvents at indicated volumes at 25-30° C. and stirred for 10 minutes. This slurry was heated for complete dissolution and anti-solvent was added to the reaction mass to isolate O-Desmethylvenlafaxine succinate Form-I.

| Process | Solvents | Total volume | Volume ratio | Temp (° C.) | Result |
|---|---|---|---|---|---|
| Antisolvent method | ACN/IPE | 50 | 1:2 | 80-90 | Form I |
| | Xylene/Acetone | 100 | 1:2 | 140-150 | Form I |

EXAMPLE 7

Preparation of O-Desmethylvenlafaxine Succinate Form-I 1 g of O-Desmethylvenlafaxine free base and 0.45 g of succinic acid was suspended in indicated solvents at indicated volumes at 25-30° C. and stirred for 10 minutes. This slurry was heated for complete dissolution and rapidly cooled to −35° C. and stirred for 30 min. The solid obtained was filtered to give crystalline O-Desmethylvenlafaxine Succinate Form-I. The specific reaction conditions and results obtained are displayed in below table.

| Process | Solvents | Volume ratio | Temp (° C.) | Result |
|---|---|---|---|---|
| Fast Cooling | THF | 1:50 | −35 | Form I |
| | IPA | 1:50 | −35 | Form I |

EXAMPLE 8

Preparation of O-Desmethylvenlafaxine Succinate Form-I 1 g of O-Desmethylvenlafaxine free base was suspended in THF (80 ml) at 25-30° C. and stirred for 10 minutes. 0.45 g of succinic acid was added to the reaction mass and heated to 60-70° C. The reaction mass was stirred for 10 min at same temperature and filtered through cotton to remove any undissolved solid particulates. The clear solution obtained was then transferred to petri dish to evaporate the solvent rapidly at ambient temperature to give O-Desmethylvenlafaxine Succinate Form-I.

EXAMPLE 9

Preparation of O-Desmethylvenlafaxine Succinate Form-II 1 g of O-Desmethylvenlafaxine free base and 0.45 g of succinic acid was suspended in indicated solvents at indicated volumes at 25-30° C. and stirred for 10 minutes. This slurry was heated for complete dissolution and allowed for crystallization at room temperature. The solid obtained was filtered to give O-Desmethylvenlafaxine Succinate Form-II. The specific reaction conditions and results obtained are displayed in below table.

| Process | Solvents | Volume ratio | Temp (° C.) | Result |
|---|---|---|---|---|
| Slow Crystallization | Methanol | 1:80 | 50-60 | Form II |
| | 1,4-dioxane | 1:80 | 100-110 | Form II |
| | Acetonitrile | 1:50 | 80-90 | Form II |

EXAMPLE 10

Preparation of O-Desmethylvenlafaxine Succinate Form-II

O-Desmethylvenlafaxine base (100 g) was suspended in isopropyl alcohol (500 ml) and water (10 ml). Succinic acid was added to the reaction mass slurry and heated to 65-70° C. for complete dissolution. The reaction mass was cooled to 0-10° C. The reaction mass was filtered and washed with isopropyl alcohol to give O-Desmethylvenlafaxine succinate solid, which was dissolved in isopropyl alcohol (1200 ml) and heated to 60-80° C. The reaction mass was cooled to 20-30° C. and filtered to give O-Desmethylvenlafaxine succinate Form-II.

EXAMPLE 11

Preparation of O-Desmethylvenlafaxine Succinate Form-II 5 g of O-Desmethylvenlafaxine free base was suspended in indicated solvents at indicated volumes at 25-30° C. and stirred for 10 minutes. This slurry was heated to reflux temperature for complete dissolution. In another flask (2.8 g) of succinic acid was dissolved in indicated solvents at indicated volumes at 25-30° C. and slowly added to the free-base solution at reflux temperature and maintained for 1-3 hrs. The reaction mass was then cooled to room temperature. The solid obtained was filtered to give crystalline O-Desmethylvenlafaxine Succinate Form-II. The specific reaction conditions and results obtained are displayed in below table.

| Input | Solvents | Volume ratio | Temp. (° C.) | Time | Result |
|---|---|---|---|---|---|
| Free base and Succinic acid | Acetonitrile | 1:50 | 80-90 | 2 hrs | Form II |
| | Ethyl acetate | 1:50 | 70-80 | 1 hr | Form II |
| | Isopropyl alcohol | 1:15 | 80-90 | 30 min | Form II |
| | n-Propanol | 1:1.5 | 90-100 | 1 hr | Form II |
| | n-BuOH | 1:15 | 110-120 | 1 hrs | Form II |
| | CHCl$_3$ | 1:50 | 55-60 | 1 hr | Form II |
| | IPA/Cyclohexane | 1:4 | 80-90 | 1-2 hrs | Form II |

EXAMPLE 12

Preparation of O-Desmethylvenlafaxine Succinate Form-II from Amorphous Form 1 g of amorphous O-Desmethylvenlafaxine Succinate was suspended in acetonitrile (50 ml) at 25-30° C. and stirred for 30 minutes. The solid obtained was filtered to give crystalline O-Desmethylvenlafaxine Succinate Form-II.

EXAMPLE 13

Preparation of O-Desmethylvenlafaxine Succinate Form-II from Amorphous Form 1 g of amorphous O-Desmethylvenlafaxine Succinate was exposed to humidity for 10 minutes at 25-30° C. The solid obtained was isolated and identified as crystalline O-Desmethylvenlafaxine Succinate Form-II.

EXAMPLE 14

Preparation of O-Desmethylvenlafaxine Succinate Form-III 1 g of O-Desmethylvenlafaxine free base is suspended in indicated solvents at indicated volumes at 25-30° C. and stirred for 10 minutes. This slurry was heated to reflux temperature for complete dissolution. To this clear solution indicated solvents at indicated volumes were added at 25-30° C. and maintained for 1-3 hrs. The solid obtained was filtered and identified as crystalline O-Desmethylvenlafaxine Succinate Form-III. The specific reaction conditions and results obtained are displayed in below table.

| Process | Solvents | Total volume | Volume ratio | Temp (° C.) | Result |
|---|---|---|---|---|---|
| Antisolvent method | Toluene/Acetone | 10 | 1:1 | 110-120 | Form III |
| | Toluene/ACN | 10 | 2:1 | 85-90 | Form III |

EXAMPLE 15

Preparation of Amorphous O-Desmethylvenlafaxine Succinate 1 g of O-Desmethylvenlafaxine free base was suspended in ethanol (50 ml) at 25-30° C. and stirred for 10 minutes. 0.45 g of succinic acid was added and heated to 60-70° C. The reaction mass was stirred for 10 min at same temperature and filtered through cotton to remove any undissolved solid particulates. The clear solution obtained was then distilled under vacuum at 40-45° C. Acetonitrile (70 ml) was added

| Process | Solvents | Total volume | Volume ratio | Temp (° C.) | Result |
|---|---|---|---|---|---|
| Antisolvent method | Toluene/Acetone | 10 | 1:1 | 110-120 | Form III |
| | Toluene/ACN | 10 | 2:1 | 85-90 | Form III | to the reaction mass and was heated to obtain a clear solution. The clear solution was then further distilled under vacuum at 40-45° C. Solid obtained was isolated under nitrogen atmosphere to give amorphous O-Desmethylvenlafaxine Succinate.

EXAMPLE-16

Preparation of O-Desmethylvenlafaxine (Demethylation)

5.0 g Venlafaxine was dissolved in 50 ml dimethylsulfoxide at 25-30° C. Sodium cyanide 9.0 g was added and reaction mass was heated to 180-185° C. for 4 hours. The reaction mass was cooled and 25 ml water was added. The resulting solution was extracted with 2×50 ml ethyl acetate, combined organic layer was dried over anhydrous sodium sulfate, followed by distillation to give residue. The residue was treated with 25 ml acetone then cooled to 0-5° C. to give O-desmethylvenlafaxine.

We claim:
1. A process for the preparation of O-Desmethylvenlafaxine succinate Form-II, comprising the steps of:
   a) dissolving O-Desmethylvenlafaxine base in a solvent,
   b) heating the reaction mass to reflux,
   c) adding succinic acid,
   d) cooling the reaction mass, and
   e) isolating O-Desmethylvenlafaxine succinate Form-II.
2. The process according to claim 1, wherein the solvent is selected from acetonitrile, chloroform, ethyl acetate, isopropyl alcohol, n-propanol, n-butanol, cyclohexane or mixture thereof.
3. The process according to claim 1, wherein the succinic acid is selected from solid succinic acid or succinic acid solution.
4. The process according to claim 1, wherein the O-Desmethylvenlafaxine base is a solid or a liquid solution.

* * * * *